(12) United States Patent
Sato

(10) Patent No.: US 12,357,265 B2
(45) Date of Patent: Jul. 15, 2025

(54) ULTRASOUND DIAGNOSTIC APPARATUS

(71) Applicant: Canon Medical Systems Corporation, Otawara (JP)

(72) Inventor: Takeshi Sato, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 0 days.

(21) Appl. No.: 18/517,039

(22) Filed: Nov. 22, 2023

(65) Prior Publication Data

US 2024/0173008 A1 May 30, 2024

(30) Foreign Application Priority Data

Nov. 24, 2022 (JP) .................. 2022-187722

(51) Int. Cl.
*A61B 8/06* (2006.01)
*A61B 8/00* (2006.01)
*G01S 15/89* (2006.01)

(52) U.S. Cl.
CPC .............. *A61B 8/06* (2013.01); *A61B 8/4488* (2013.01); *A61B 8/488* (2013.01); *G01S 15/8995* (2013.01); *A61B 8/461* (2013.01)

(58) Field of Classification Search
CPC ......... A61B 8/06; A61B 8/4488; A61B 8/488; A61B 8/461; A61B 8/5223; A61B 8/5246; A61B 8/5207; A61B 8/5269; A61B 8/54; A61B 8/44; A61B 8/4444; A61B 8/52; G01S 15/8995; G01S 15/8977; G01S 15/8986
See application file for complete search history.

(56) References Cited

U.S. PATENT DOCUMENTS

| 10,993,698 B2 | 5/2021 | Sato |
| 11,564,662 B2 | 1/2023 | Sato |
| 11,583,241 B2 | 2/2023 | Sato |

(Continued)

FOREIGN PATENT DOCUMENTS

| EP | 3 613 349 A1 | 2/2020 |
| JP | 2015-217172 A | 12/2015 |

(Continued)

OTHER PUBLICATIONS

Montaldo et al., "Coherent Plane-Wave Compounding for Very High Frame Rate Ultrasonography and Transient Elastography", IEEE Transactions on Ultrasonics, Ferroelectrics, and Frequency Control, vol. 56, No. 3, 2009 18 pages.

(Continued)

*Primary Examiner* — Bo Joseph Peng
(74) *Attorney, Agent, or Firm* — Oblon, McClelland, Maier & Neustadt, L.L.P.

(57) ABSTRACT

An ultrasound diagnostic apparatus repeats ultrasonic wave transmissions with different transmission angles in units of packets. The apparatus receives reception signals. The apparatus performs beamforming on the reception signals. The apparatus performs MTI filtering on initial images for each group of the same transmission angle. The apparatus performs principal component analysis on the MTI images for each of the packets having the same set of transmission angles. The apparatus performs coherent addition on the principal component images for each of the packets to generate coherent addition images.

10 Claims, 10 Drawing Sheets

(56) References Cited

U.S. PATENT DOCUMENTS

| | | | |
|---|---|---|---|
| 2010/0016723 A1* | 1/2010 | Imamura | A61B 8/06 600/443 |
| 2014/0039317 A1* | 2/2014 | Sato | A61B 8/5246 600/443 |
| 2015/0327840 A1 | 11/2015 | Hirama et al. | |
| 2015/0366540 A1* | 12/2015 | Sato | A61B 8/5207 600/453 |
| 2016/0089115 A1* | 3/2016 | Sato | A61B 8/06 600/447 |
| 2017/0071569 A1* | 3/2017 | Sato | G01S 7/52033 |
| 2019/0209133 A1* | 7/2019 | Takahashi | A61B 8/5207 |

FOREIGN PATENT DOCUMENTS

| | | |
|---|---|---|
| JP | 2017-55845 A | 3/2017 |
| JP | 2017-55846 A | 3/2017 |
| JP | 2018-122082 A | 8/2018 |
| JP | 2019-97794 A | 6/2019 |
| JP | 2019-97795 A | 6/2019 |

OTHER PUBLICATIONS

Bercoff et al., "Ultrafast Compound Doppler Imaging: Providing Full Blood Flow Characterization", IEEE Transactions on Ultrasonics, Ferroelectrics, and Frequency Control, vol. 58, No. 1, 2011, 14 pages.

Hasegawa et al., "High-frame-rate echocardiography using diverging transmit beams and parallel receive beamforming", Journal of Medical Ultrasonics, vol. 38, 2011, 12 pages.

Bendjador et al., "The SVD Beamformer: Physical Principles and Application to Ultrafast Adaptive Ultrasound", IEEE Transactions on Medical Imaging, vol. 39, No. 10, 2020, 13 pages.

* cited by examiner

ULTRASOUND DIAGNOSTIC APPARATUS

CROSS-REFERENCE TO RELATED APPLICATIONS

This application is based upon and claims the benefit of priority from Japanese Patent Application No. 2022-187722, filed Nov. 24, 2022, the entire contents of which are incorporated herein by reference.

FIELD

Embodiments described herein relate generally to an ultrasound diagnostic apparatus.

BACKGROUND

As an ultrasound imaging technique, coherent plane wave compounding (CPWC) has been known, with which plane waves incident at different transmission angles are coherently summed. CPWC has been applied to color Doppler imaging. Although CPWC, which offers both a high frame rate and a high resolution, is an effective technique, artifacts tend to be generated horizontally or in an arc shape in a wide range in the presence of a specular reflector. These artifacts are remarkable in color Doppler imaging, for which ultrasonic waves are repeatedly transmitted to the same space.

DETAILED DESCRIPTION

An ultrasound diagnostic apparatus according to the present embodiment includes a transmission unit, a reception unit, a beamforming unit, a filter unit, a principal component analysis unit, and a coherent addition unit. The transmission unit repeats ultrasound transmissions with different transmission angles and/or different transmission origins in units of packets by way of an ultrasonic probe provided with a plurality of transducers. The reception unit receives a plurality of reception signals respectively corresponding to the ultrasound transmissions by way of this ultrasonic probe. The beamforming unit performs a beamforming process on the reception signals to generate a plurality of initial images. The filter unit performs an MTI filtering process on the initial images for each group of the same transmission angle and/or the same transmission origin to generate a plurality of MTI images. The principal component analysis unit performs a principal component analysis on the MTI images for each of the packets with the same set of transmission angles and/or transmission origins to generate a plurality of principal component images. The coherent addition unit performs a coherent addition on the principal component images for each packet to generate a plurality of coherent addition images.

The ultrasound diagnostic apparatus according to the present embodiment will be described in detail below with reference to the drawings.

Figure 1:
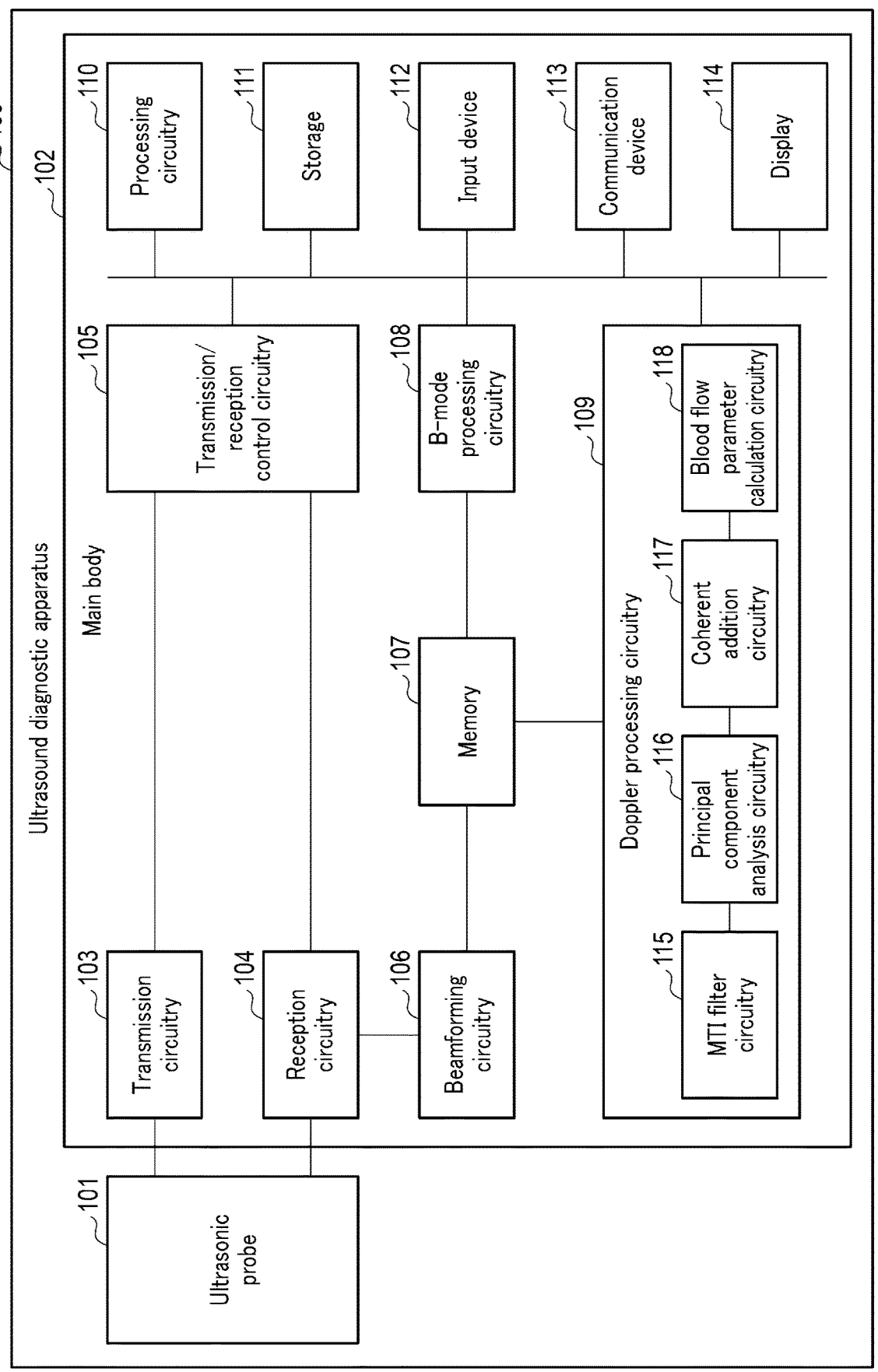
FIG. 1 is a diagram showing an exemplary structure of an ultrasound diagnostic apparatus according to the present embodiment.

FIG. 1 is a diagram for showing an exemplary structure of an ultrasound diagnostic apparatus 100 according to the present embodiment. As illustrated in FIG. 1, the ultrasound diagnostic apparatus 100 includes an ultrasonic probe 101 and an main body 102. The main body 102 includes transmission circuitry 103, reception circuitry 104, transmission/reception control circuitry 105, beamforming circuitry 106, a memory 107, B-mode processing circuitry 108, Doppler processing circuitry 109, processing circuitry 110, a storage 111, a display 114, an input device 112, and a communication device 113. The ultrasonic probe 101 is detachably coupled to the main body 102.

The ultrasonic probe 101 is a probe configured to transmit and receive ultrasonic waves and is provided with a plurality of transducers that are one-dimensionally or two-dimensionally aligned. Each transducer transmits ultrasonic waves in response to a drive signal supplied from the transmission circuitry 103. To each drive signal, a delay time is assigned such that ultrasonic waves transmitted from the entire ultrasonic probe 101 can be concentrated on a specific wavefront. The emitted ultrasonic waves are reflected upon the surface of mismatched acoustic impedances inside the target patient's body. Each of the transducers receives the ultrasonic wave (reflection wave) reflected inside the target patient's body and converts it to an echo signal. The ultrasonic probe 101 may be a linear probe, a convex probe, a sector probe, or a probe of any other alignment.

The transmission circuitry 103 repeats transmission of multiple ultrasonic waves with different transmission angles and/or different transmission origins in units of packets by way of the ultrasonic probe 101 having multiple transducers. In particular, under the control of the transmission/reception control circuitry 105, the transmission circuitry 103 supplies drive signals with delay times respectively assigned to the transducers so as to perform ultrasound transmissions at different transmission angles and/or from different transmission origins. The transmission circuitry 103 repeats the transmissions in such a manner that the regions of transmission space will overlap each other. Examples of the ultrasonic wave transmission according to the present embodiment include a plane wave transmission, diffusion wave transmission, and distant focus transmission.

The reception circuitry 104 receives, by way of the ultrasonic probe 101, reception signals respectively corresponding to the ultrasonic waves transmitted by the transmission circuitry 103. In particular, the reception circuitry 104 is connected to the transducers provided in the ultrasonic probe 101. Each transducer corresponds to each channel. The reception circuitry 104 includes amplification circuitry, A/D conversion circuitry, and DC wave detection circuitry for each channel. The amplification circuitry amplifies echo signals from the transducers and performs a gain correction process thereon. The A/D conversion circuitry performs an A/D conversion on the gain-corrected echo signals. The DC wave detection circuitry converts a digital echo signal into an in-phase signal (I signal) and quadrature signal (Q signal) within a baseband. When an I signal and a Q signal do not need to be distinguished from each other, they will simply be referred to as reception signals. The reception signals are supplied to the beamforming circuitry 106.

The transmission/reception control circuitry 105 synchronously controls the transmission circuitry 103 and reception circuitry 104 such that ultrasonic scanning can be executed using transmission of ultrasonic waves at different transmission angles and/or from different transmission origins.

The beamforming circuitry 106 performs a beamforming process on respective reception signals to generate initial images. That is, the beamforming circuitry 106 generates one initial image in correspondence with one ultrasonic transmission. Each initial image represents a spatial distribution of reflection wave intensity values in the reception area, which corresponds to one ultrasonic transmission. Examples of such beamforming include pixel beamforming. With the pixel beamforming, complex pixel values of the pixels located at the same position in the space can be calculated, without depending on a transmission angle and/or transmission start point. The beamforming circuitry 106 can be realized by any processor.

The memory 107 stores data of initial images. As the memory 107, any storage may be adopted such as a Random Access Memory (RAM), a Read Only Memory (ROM), or a semiconductor memory device.

The B-mode processing circuitry 108 reads an initial image from the memory 107 and executes a B-mode process on this image to generate a B-mode image. Each pixel of the B-mode image expresses the signal intensity of a reflection wave with a brightness value. The B-mode processing circuitry 108 can be realized by any processor.

The Doppler processing circuitry 109 reads an initial image from the memory 107 and executes a color Doppler process on this image to generate a blood flow image. The Doppler processing circuitry 109 according to the present embodiment generates a blood flow image, from which artifacts that have been generated by specular reflection echo in the blood flow components are reduced. As illustrated in FIG. 1, the Doppler processing circuitry 109 includes MTI filter circuitry 115, principal component analysis circuitry 116, coherent addition circuitry 117, and blood flow parameter calculation circuitry 118. The MTI filter circuitry 115, principal component analysis circuitry 116, coherent addition circuitry 117, and blood flow parameter calculation circuitry 118 may be realized by any processor.

The MTI filter circuitry 115 performs moving target indicator (MTI) filtering on initial images for every group of the same transmission angle and/or the same transmission origin to generate a plurality of MTI images. The principal component analysis circuitry 116 analyzes the principal components of the MTI images for each packet of the same transmission angle set and/or the same transmission origin set to generate a plurality of principal component images. The coherent addition circuitry 117 performs a coherent addition on the principal component images for each packet to generate a plurality of coherent addition images. The blood flow parameter calculation circuitry 118 performs a blood flow parameter calculation process on the coherent addition images to generate a blood flow image representing a spatial distribution of blood flow parameters. The blood flow parameter calculation circuitry 118 performs a power addition process on the coherent addition images to generate, as a blood flow image, a blood flow power image representing the spatial distribution of blood flow power, which is a blood flow parameter. A blood flow parameter, if not blood flow power, may be the velocity or variance of the blood flow.

The processing circuitry 110 includes a process such as a central processing unit (CPU) that centralizes the control of the ultrasound diagnostic apparatus 100. The processing circuitry 110 executes an ultrasonic diagnostic program stored in the storage 111 to control the transmission/reception control circuitry 105, B-mode processing circuitry 108, Doppler processing circuitry 109, storage 111, input device 112, communication device 113, and display 114. In one example, the processing circuitry 110 may display on the display 114 a blood flow image generated by the blood flow parameter calculation circuitry 118. The processing circuitry 110 is an example of a display control unit.

The storage 111 is a storage for storing various kinds of data, such as a ROM, a RAM, a hard disk drive (HDD), a solid state drive (SSD), and an integrated circuit storage. The storage 111 may also be, for example, a drive assembly that performs reading and writing of various kinds of information on a portable storage medium such as a CD-ROM drive, a DVD drive, or a flash memory. For instance, the storage 111 may store the ultrasonic diagnostic program or the like of the ultrasound diagnostic apparatus 100.

The input device 112 can be various types of user interfaces on a touch panel or an operational panel. An operator may input various operations and commands to the ultrasound diagnostic apparatus 100 via the input device 112. The input device 112 may be a speech recognition device that converts audio signals collected by a microphone into command signals.

The communication device 113 is a communication interface for data communications with a Picture Archiving and Communication System (PACS) server, a Hospital Information System (HIS) server, a Modality Worklist Management (MWM) server and the like via a local area network (LAN).

The display 114 displays various kinds of data in accordance with commands from the processing circuitry 110. As a display 114, a CRT display, a liquid crystal display (LCD), a Cathode Ray Tube (CRT) display, an organic electro luminescence display (OELD), a plasma display, or any other display can be adopted as appropriate. A projector may also be adopted as a display 114.

The ultrasound diagnostic apparatus 100 according to the present embodiment will be described in detail below. In the description, a plane wave transmission will be considered as a type of ultrasonic wave transmission. In the plane wave transmission, the transmission circuitry 103 performs multiple plane wave transmissions at different deflection angles, as ultrasound transmissions with different transmission angles and/or different transmission origins. A deflection angle is defined by an angle formed by the central axis of a plane wave and a transducer surface of the transducer set.

Artifacts generated by a specular reflector (hereinafter referred to as specular reflector artifacts) are the reduction target of the present embodiment, and these artifacts will be explained below.

Figure 2:
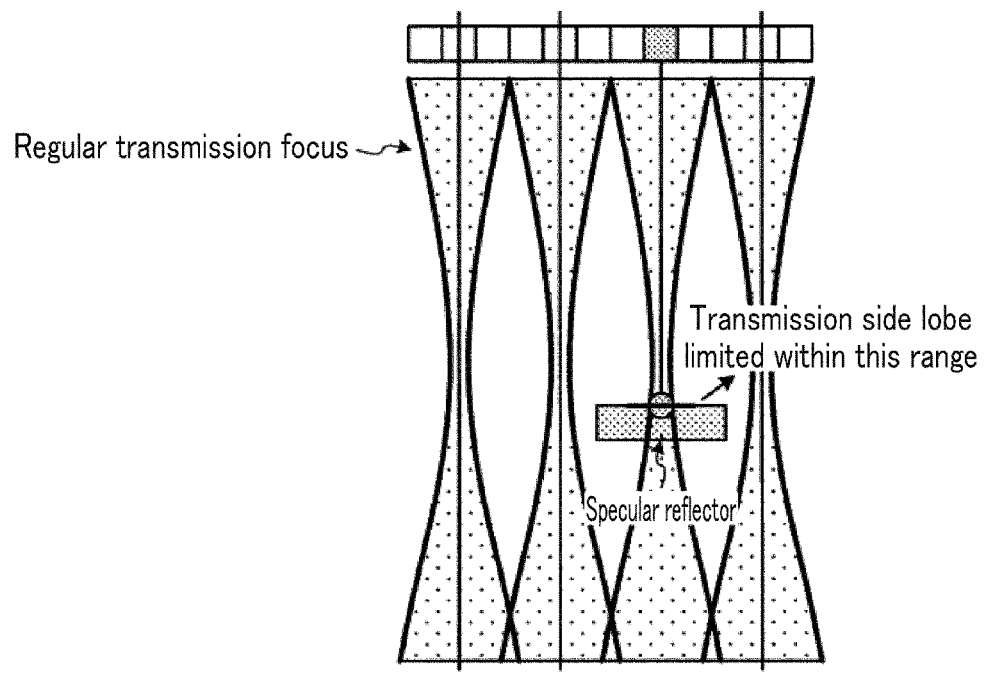
FIG. 2 is a diagram for explaining the mechanism for specular reflector artifact production when the transmission focus is attained.
Figure 3:
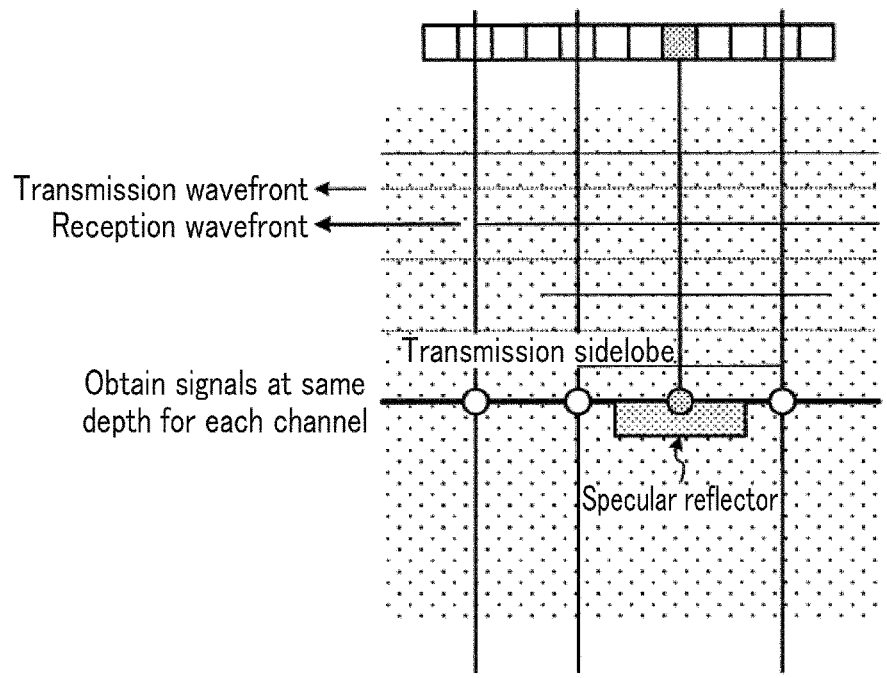
FIG. 3 is a diagram for explaining the mechanism for specular reflector artifact production at the time of plane wave transmission.

FIG. 2 is a diagram for explaining the mechanism for specular reflector artifact generation when the transmission focus is attained. FIG. 3 is a diagram for explaining the mechanism for specular reflector artifact generation at the time of plane wave transmission. As illustrated in FIG. 2, where a transmission focus is attained, a high-intensity echo from the specular reflector appears as artifacts only within a transmission focused range. As illustrated in FIG. 3, however, where a plane wave transmission is conducted, artifacts are generated across a much broader area.

Figure 4:
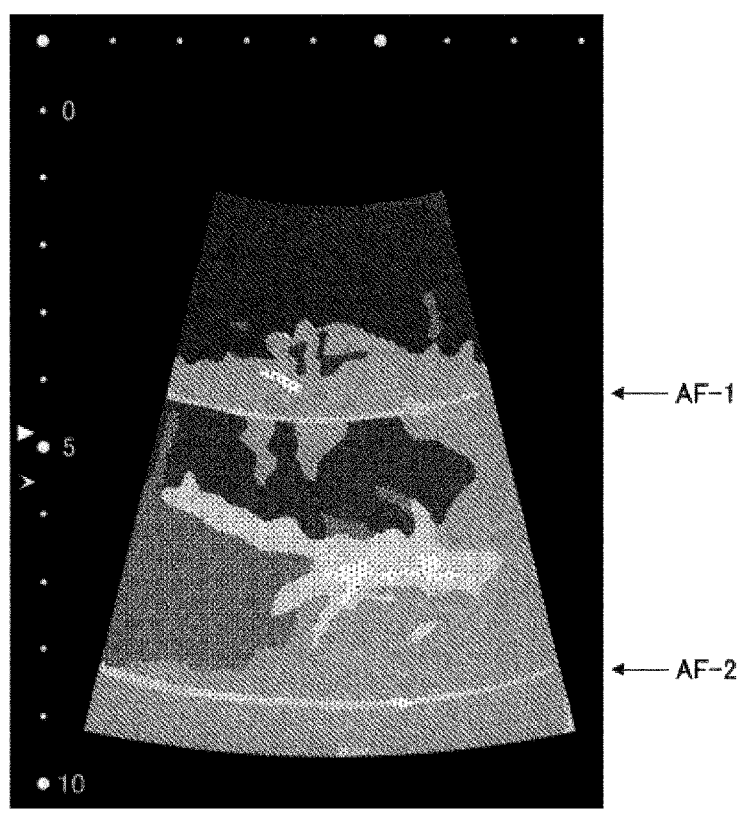
FIG. 4 is a diagram for exemplifying a blood flow image displayed in a power display mode, the blood flow image being obtained by color Doppler imaging through a plane wave transmission in a single direction.

FIG. 4 is a diagram exemplifying a blood flow image displayed in a power display mode, where the blood flow image is obtained by color Doppler imaging through a plane wave transmission in a single direction. In FIG. 4, arc-shaped specular reflector artifacts AF-1 and AF-2 appear in the blood flow image. These specular reflector artifacts AF-1 and AF-2 are caused by specular reflection at a portion with the highest brightness in the arc-shaped image. The specular reflector artifacts AF-1 and AF-2 tend to be caused at a cardiac valve, cardiac wall, diaphragm, and the like. These artifacts will not disappear even by conducting coherent plane wave compounding (CPWC) of multiple deflection angles. This is because an echo from the specular reflector is too strong to erase even by adding data of other deflection angles.

Figure 5:
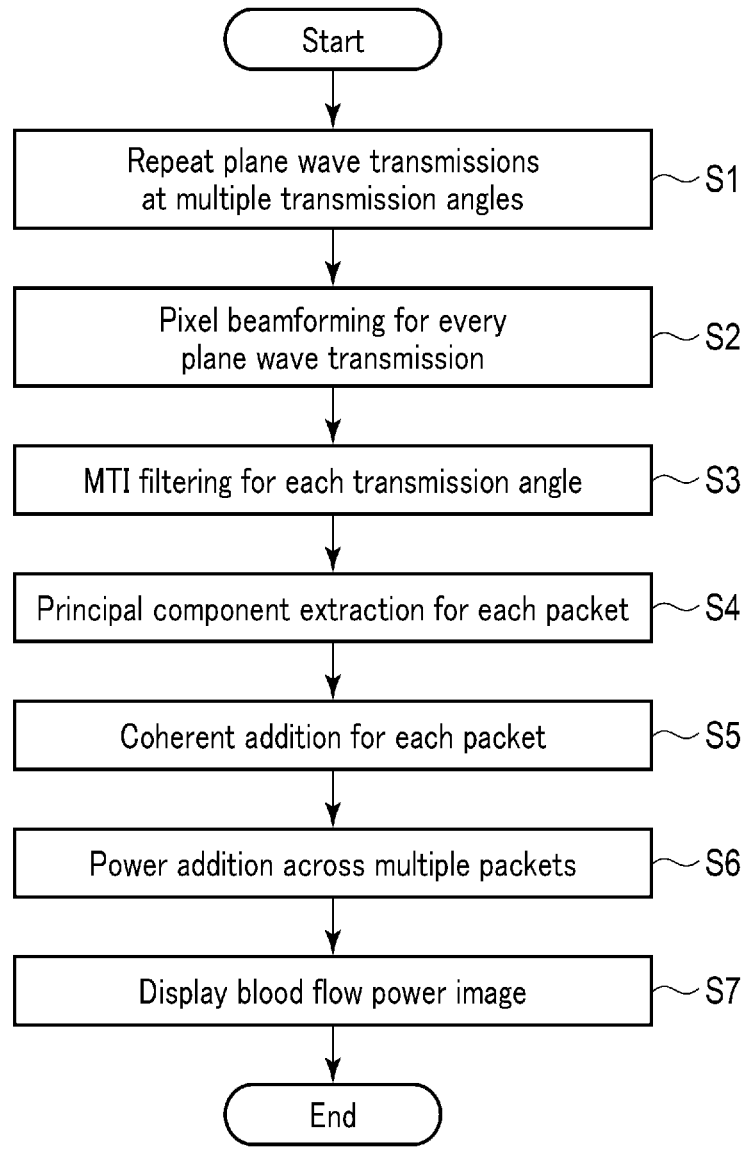
FIG. 5 is a diagram showing the processing procedure of ultrasonography performed by the ultrasound diagnostic apparatus according to the present embodiment.
Figure 6:
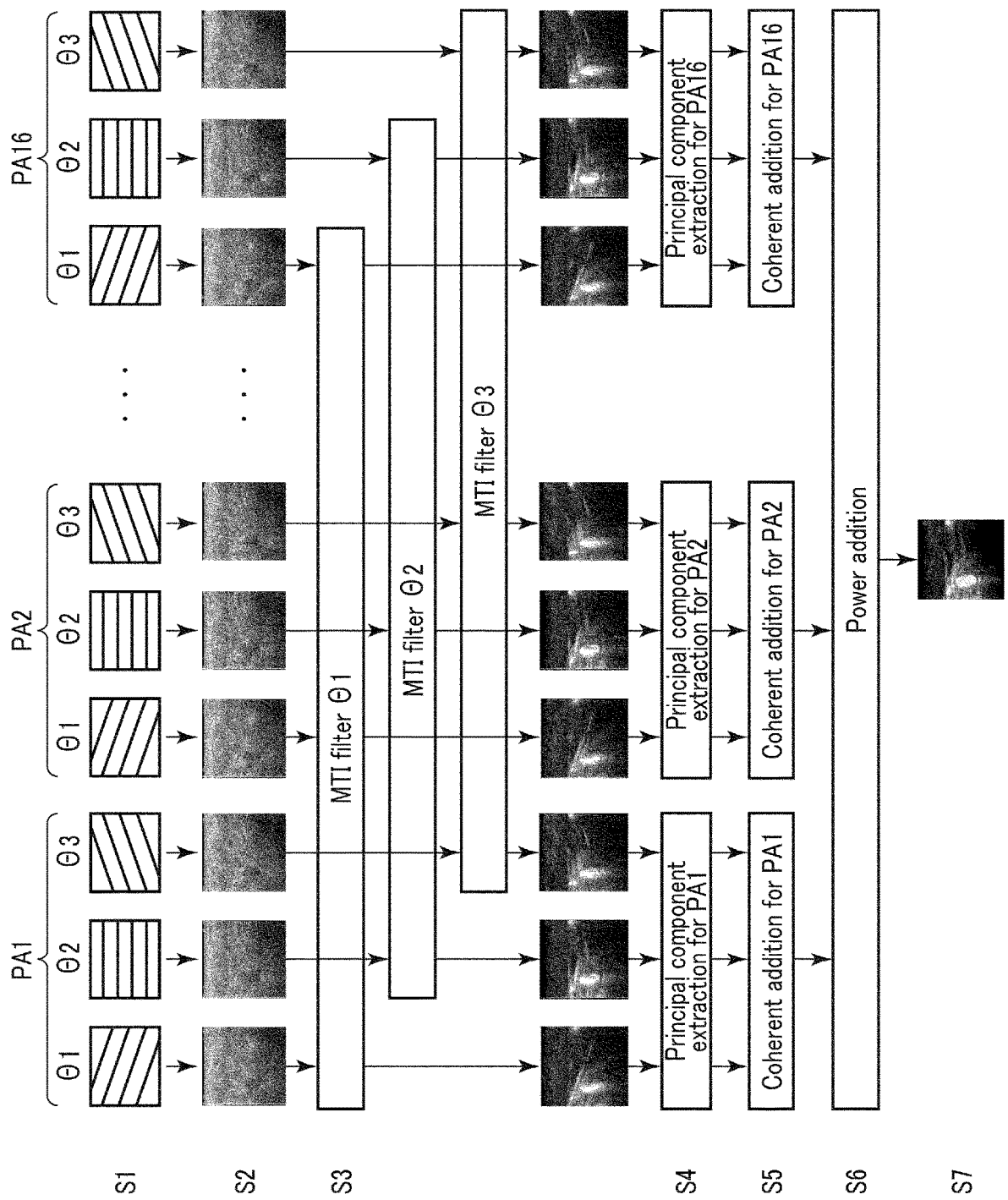
FIG. 6 is a diagram schematically showing the processing procedure of the ultrasonography illustrated in FIG. 5.

FIG. 5 is a diagram showing the processing procedure of ultrasonography performed by the ultrasound diagnostic apparatus 100 according to the present embodiment. FIG. 6 is a diagram schematically showing the processing procedure of the ultrasonography illustrated in FIG. 5. In the example of FIG. 6, the plane wave transmissions are performed using three different directions and 16 packets. A "packet" refers to a set of sequentially conducted plane wave transmissions using one of multiple transmission angles in turn, and data pieces respectively corresponding to these plane wave transmissions. In the example of FIG. 6, plane waves of three different directions are transmitted per packet, and 16 packets are required to generate a single blood flow image. This number will be referred to as a processing target number of packets. The number of plane wave transmissions per packet and the processing target number of packets are not limited to the above example, however, and can be set to any suitable numbers.

As illustrated in FIGS. 5 and 6, the transmission circuitry 103 repeats plane wave transmissions at multiple transmission angles (step S1). In the example of FIG. 6, under the control of the transmission/reception control circuitry 105, the transmission circuitry 103 repeatedly and sequentially transmits plane waves at three transmission angles θ1, θ2, and θ3 through the ultrasonic probe 101. That is, three plane wave transmissions respectively corresponding to the three transmission angles θ1, θ2, and θ3 form one packet, and multiple packets of ultrasonic wave transmissions are repeatedly conducted. Between these packets, the set of transducers that transmit the plane waves may differ, or in other words, scanning regions may differ. Plane waves are reflected upon the body tissues of a subject. The reflection waves are converted to echo signals by the ultrasonic probe 101. An echo signal is converted to a reception signal by the reception circuitry 104. One reception signal corresponds to one plane wave transmission.

Three plane waves of the transmission angles θ1, θ2, and θ3 in one packet PA are transmitted in such a manner that the target regions of transmission space overlap each other. The transmission angle θ is defined as an angle formed by the plane wave and the transmission surface of the transducer set of the ultrasonic probe 101. The transmission angle θ2 is determined as the transmission angle θ=0. The transmission angle θ1 is larger than the transmission angle θ2, while the transmission angle θ3 is smaller than the transmission angle θ2. The number of transmission angles θ is not limited to 3, and can be any number equal to or larger than 2.

After step S1, the beamforming circuitry 106 executes pixel beamforming on every plane wave transmission (step S2). The pixel beamforming is a process performed by a beamformer calculating a complex pixel value of pixels that are located at the same spatial position regardless of the transmission angle. At step S2, the beamforming circuitry 106 executes the pixel beamforming on a reception signal for each plane wave transmission to generate an initial image.

After step S2, the MTI filter circuitry 115 executes MTI filtering for each transmission angle (step S3). At step S3, among the chronologically generated initial images, the MTI filter circuitry 115 selects, as processing targets, initial images that belong to the processing target number of packets (16 packets in FIG. 6) preceding and including the current packet. The MTI filter circuitry 115 executes MTI filtering on the initial images selected as processing targets. Steps S3 to S7 are executed every time the ultrasonic wave transmission of a new packet is conducted.

In particular, the MTI filter circuitry 115 collects, from the processing target initial images, initial images that belong to a group of the same transmission angle and correspond to the processing target number of packets, and executes MTI filtering thereon. For instance, if the packet PA16 is a processing target packet and the processing target transmission angle is θ2, initial images of the transmission angle θ2 are collected from the most recent 16 packets PA16 to PA1, and the 16 initial images relating to the transmission angle θ2 are subjected to the MTI filtering. The MTI filter circuitry 115 thereby outputs images subjected to the MTI filtering (MTI images). MTI images are generated for each transmission angle in each packet.

An MTI filter is configured to extract only blood flow components by removing tissue components from the image data. The MTI filter is realized by a high-pass filter relating to a packet direction. The packet direction corresponds to the chronological or reverse chronological direction of the transmission times. As the MTI filter, a filter configured to analyze the principal components with respect to the packet direction and output components other than the principal ones as blood flow components may be adopted.

After step S3, the principal component analysis circuitry 116 executes a principal component extraction for each packet (step S4). In particular, at step S4, the principal component analysis circuitry 116 executes a principal component analysis with respect to a transmission angle θ on the MTI images generated at step S3 for each packet PA to extract the principal components. For instance, the principal component extraction process is conducted on the MTI image of the transmission angle θ1, the MTI image of the transmission angle θ2, and the MTI image of the transmission angle θ3 in the packet PA16. With the principal component extraction process, specular reflector artifacts generated due to a peculiar echo intensity with respect to a transmission angle can be reduced. An image of an extracted principal component is output as a principal component image.

The processing procedure of the principal component analysis at step S4 is indicated below. Initially, the input signal vector $x_{i,j}$ at step S4 is expressed in Equation (1) below. This input signal vector $x_{i,j}$ indicates a vector expression of the pixel value of an MTI image, where i=1 to NxxNz, with Nx representing the number of data items in the azimuth direction and Nz representing the number of data items in the depth direction; j=1 to L, with L representing the number of packets, for example, 16 in the case of FIG. 6; and Ne represents the number of transmission angles, for example, 3 in the case of FIG. 6.

$$x_{i,j} = \begin{pmatrix} x(i, j, 1) \\ x(i, j, 2) \\ \vdots \\ x(i, j, N_\theta) \end{pmatrix} \quad (1)$$

Based on the input signal vector $x_{i,j}$, the principal component analysis circuitry 116 calculates the correlation matrix $R_{xx}$. The correlation matrix $R_{xx}$ is expressed by Equation (2) below, where H represents a complex conjugate transpose.

$$R_{xx} = \sum_{i=1}^{N_x \times N_z} x_{i,j} x_{i,j}^H \quad (2)$$

The principal component analysis circuitry 116 performs an eigenvalue decomposition on the correlation matrix $R_{xx}$ to find the diagonal matrix of the correlation matrix $R_{xx}$. The diagonal matrix D of the correlation matrix $R_{xx}$ is expressed by Equation (3) below. The diagonal matrix D in Equation (3) is a diagonal matrix having an eigenvalue as an on-diagonal element, and V is an orthogonal matrix.

$$R_{xx} = VDV^H \quad (3)$$

The principal component analysis circuitry 116 selects the number m (0<m<$N_\theta$) of principal components from the number $N_\theta$ of principal components included in the diagonal matrix D. From the Ne principal components, m largest principal components are selected. The diagonal matrix E formed from the selected m principal components $\lambda_i$ (0<i<m) is represented by Equation (4) below. The number m can be freely determined.

$$E = \begin{pmatrix} \lambda_1 & 0 & 0 & 0 \\ 0 & \ddots & 0 & 0 \\ 0 & 0 & \lambda_m & 0 \\ 0 & 0 & 0 & 0 \end{pmatrix} \quad (4)$$

Based on the diagonal matrix E and orthogonal matrix V, the principal component analysis circuitry 116 generates a filter (hereinafter referred to as a principal component filter) for extracting the m largest principal components. The principal component filter W is expressed by Equation (5) below. The principal component filter W is generated for each packet.

$$W = VEV^H \quad (5)$$

As indicated in Equation (6) below, the principal component analysis circuitry 116 applies the principal component filter W to the MTI image (input signal vector) $x_{i,j}$ so as to generate an image (hereinafter referred to as a principal component image) $y_{i,j}$ containing only the principal components of the MTI image.

$$y_{i,j} = W x_{i,j} \quad (6)$$

Figure 7:
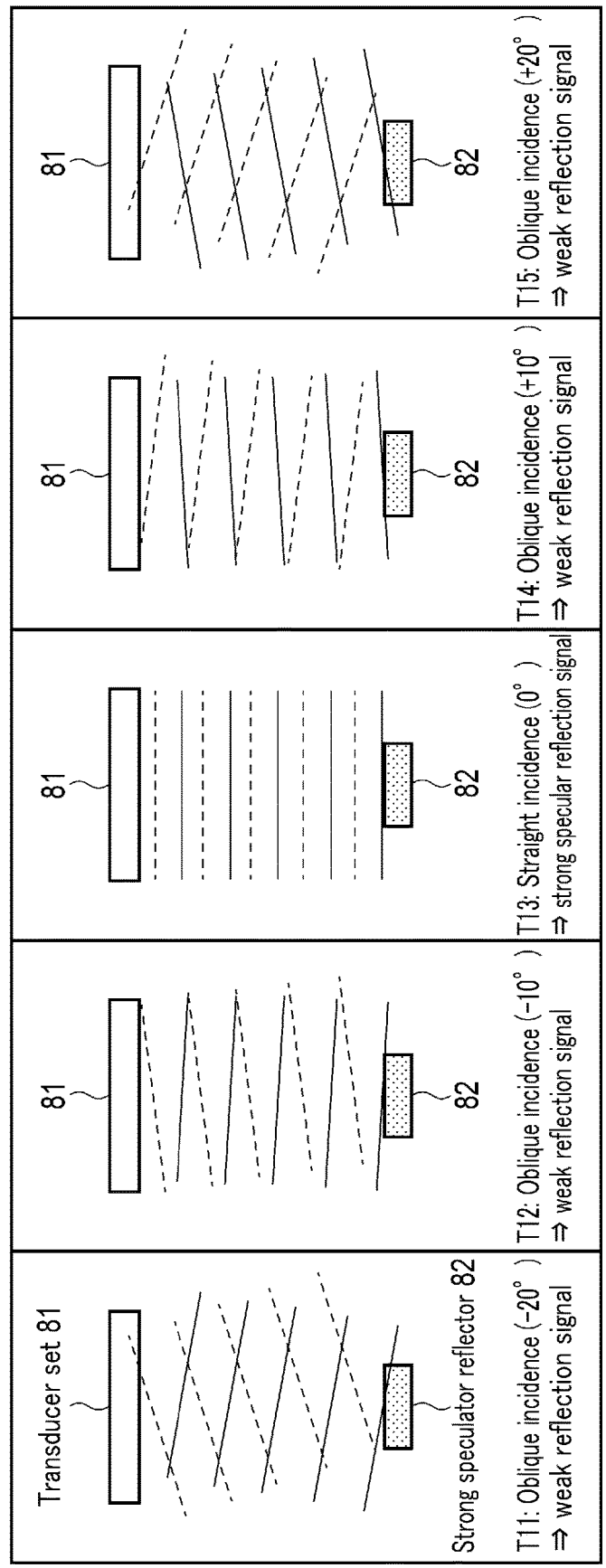
FIG. 7 is a diagram for explaining the mechanism for reduction in specular reflector artifacts through a principal component extraction process executed at step S4 of FIG. 5.

The mechanism for reduction in specular reflector artifacts through extraction of principal components will be described. FIG. 7 is a diagram for explaining the mechanism for reduction in specular reflector artifacts through the principal component extraction process. Transmission of plane waves at five different transmission angles T11 to T15 will be considered as illustrated in FIG. 7. With the transmission angle T13, where the transmission angle θ=0°, or in other words the plane wave transmitted from the transducer set 81 of the ultrasonic probe 101 is incident straight upon the specular reflector 82, a specular reflection signal with a high intensity is generated, which becomes a factor responsible for specular reflector artifacts. In contrast, with the transmission angles T11, T12, T14, and T15, where the transmission angle θ≠0°, or in other words the plane wave transmitted from the transducer set 81 is incident obliquely upon the specular reflector 82, the generated reflection signal is weak. The specular reflection signals, which exhibit a high dependency on angles, will not come out to be principal components among the reflection signals of the transmission angles T11 to T15. In this manner, specular reflector artifacts can be reduced by performing principal component filtering on the MTI images.

After step S4, the coherent addition circuitry 117 executes a coherent addition for each packet (step S5). By executing a coherent addition on a principal component image of the transmission angle θ1, a principal component image of the transmission angle θ2, and a principal component image of the transmission angle θ3 for each packet PA, the coherent addition circuitry 117 generates a coherent addition image at step S5. The coherent addition image $z_{i,j}$ is generated based on the principal component image $y_{i,j}$ in accordance with Equation (7) below, where T in the equation represents a transpose.

$$z_{i,j} = y_{i,j}^T y_{i,j} \quad (7)$$

After step S5, the blood flow parameter calculation circuitry 118 executes a power addition across multiple packets (step S6). At step S6, the blood flow parameter is set to a blood flow power. In this case, the blood flow parameter calculation circuitry 118 calculates a blood flow parameter for each pixel based on the principal component images of the transmission angles θ1 to θ3 in the 16 packets PA1 to PA16, and generates a blood flow power image that describes the spatial distribution of the blood flow parameter at step S6. The blood flow power image $P_i$ is generated based on the coherent addition image $z_{i,j}$ in accordance with Equation (8). With i=1 to Nx×Nz as mentioned earlier, the blood flow power image $P_i$ is a two-dimensional image.

$$P_i = \sum_{j=1}^{L} |z_{i,j}|^2 \quad (8)$$

After step S6, the processing circuitry 110 displays the blood flow power image (step S7). The processing circuitry 110 displays the blood flow power image generated at step S6 on the display 114 at step S7. Bloodstream power images are chronologically generated and therefore displayed as a moving image. Alternatively, a blood flow power image of a desired frame may be displayed as a still image.

Figure 8:
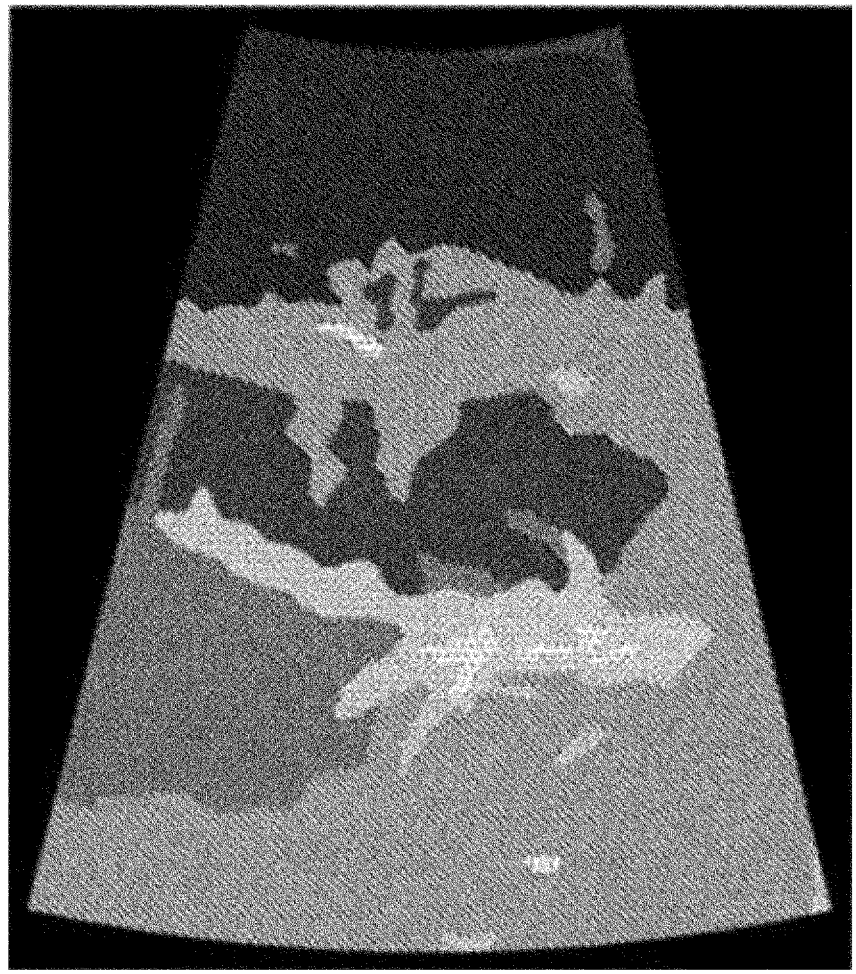
FIG. 8 is a diagram for showing an exemplary blood flow power image generated at step S6 of FIG. 5.

FIG. 8 shows an exemplary blood flow power image. A color value is assigned to each pixel of the blood flow power image in accordance with the blood flow power. As shown in FIG. 8, specular reflector artifacts are removed or reduced from the blood flow power image generated at step S6, in comparison with the blood flow power image of FIG. 4. In the same manner, blood flow images of an excellent quality with specular reflector artifacts removed or reduced can be displayed for sites in which specular reflector artifacts tend to appear, such as a cardiac valve, cardiac wall, and diaphragm. As a result, improvement in the accuracy of ultrasonic imaging diagnosis can be expected.

Figure 9:
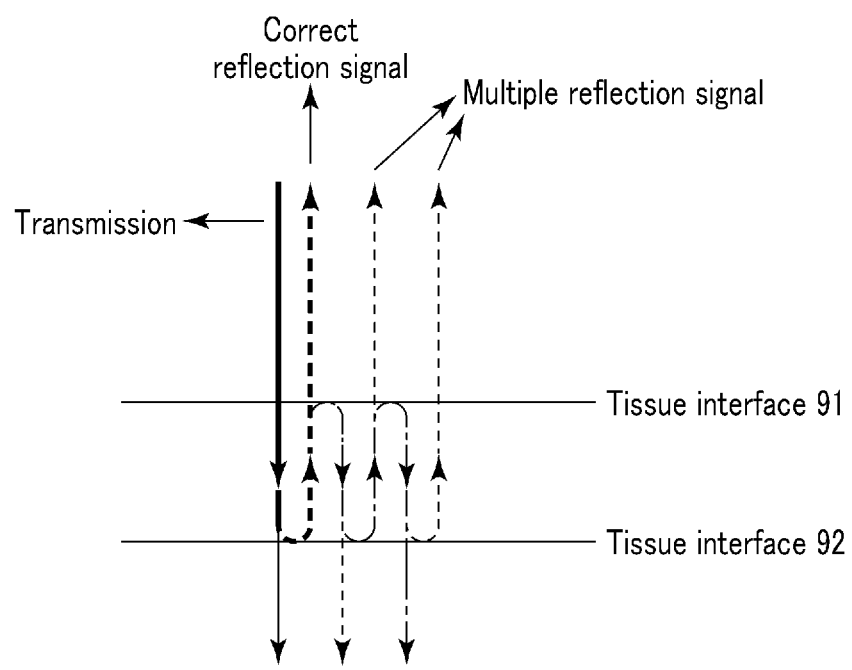
FIG. 9 is a diagram for explaining the mechanism for generation of a multiple reflection signal.

In addition to the removal of high-intensity reflection signals generated due to specular reflection, the present embodiment is effective in removal of multiple reflection as well. FIG. 9 is a diagram for explaining the mechanism for generation of a multiple reflection signal. The reflection signal that passes through the first interface 91 of tissues and is reflected upon the second interface 92 of tissues, when viewed from the ultrasonic probe 101 in FIG. 9, will be considered. In this case, the reflection wave that is reflected by the interface 92, passes through the interface 91, and is received by the ultrasonic probe 101 is considered to be the appropriate reflection signal. On the other hand, the reflection wave that is reflected by the interface 92, further reflected by the interface 91 and thereafter by the interface 92, passes through the interface 91, and is received by the ultrasonic probe 101 is considered to be a multiple reflection signal. Any reflection signal received by the ultrasonic probe 101 after multiple reciprocations between the interface 91 and interface 92 is considered to be a multiple reflection signal. Unlike a reflection signal generated by specular reflection, a multiple reflection signal exhibits a low signal level, and therefore a multiple reflection signal will not come out to be a principal component in the plane wave transmission using multiple transmission angles. Thus, the principal component extraction process according to the present embodiment can remove or reduce multiple reflection signal components.

In the above manner, the ultrasonography according to the present embodiment is completed.

The ultrasonography illustrated in FIGS. 5 and 6 is presented merely as an example. A modification, addition, and/or deletion may be suitably made within the scope of the embodiment. For instance, blood flow power images are generated in FIG. 7; however, blood velocity images with a velocity as a blood flow parameter or blood variance images with a variance as a blood flow parameter may be generated and displayed. In another example, the B-mode processing circuitry 108 may execute a B-mode process on an initial image in parallel to steps S3 to S6 to generate a B-mode image. In this case, a blood flow power image may be superimposed on, or arranged next to, the B-mode image on a display.

As described above, the ultrasound diagnostic apparatus according to the present embodiment includes transmission circuitry 103, reception circuitry 104, beamforming circuitry 106, MTI filter circuitry 115, principal component analysis circuitry 116, and coherent addition circuitry 117. The transmission circuitry 103 repeats transmission of multiple ultrasonic waves with different transmission angles and/or different transmission origins in units of packets through the ultrasonic probe 101 having multiple transducers. The reception circuitry 104 receives a plurality of reception signals respectively corresponding to the ultrasonic wave transmissions through the ultrasonic probe 101. The beamforming circuitry 106 performs a beamforming process on individual reception signals to generate a plurality of initial images. The MTI filter circuitry 115 performs an MTI filtering process on the initial images to generate a plurality of MTI images for each group of the same transmission angle and/or the same transmission origin. The principal component analysis circuitry 116 performs a principal component analysis on the MTI images for each packet including the same transmission angle set and/or the same transmission origin set to generate a plurality of principal component images. The coherent addition circuitry 117 performs a coherent addition on the principal component images for each packet to generate coherent addition images.

With the above structure, specular reflector artifacts that are highly dependent on the ultrasonic transmission angles can be removed or reduced through the analysis of principal components across the transmission angles. In addition, the analysis of principal components is conducted with respect to the transmission angles after beamforming is conducted for each ultrasonic wave transmission, which can lighten the calculation load.

Furthermore, in case of transmitting plane waves as ultrasonic waves, the analysis of principal components is conducted over multiple deflection angles. In this manner, specular reflector artifacts can be removed or reduced from the blood flow images obtained through CPWC color Doppler imaging.

Modification Example 1

In the above embodiment, a plane wave transmission is adopted as the ultrasonic wave transmission. According to the first modification example, a diffusion wave transmission is adopted as the ultrasonic wave transmission. The ultrasound diagnostic apparatus 100 according to the first modification example will be described below. In the explanation below, structural elements having substantially the same operations as the ones in the embodiment will be denoted by the same reference symbols, and the explanation of such elements will be given only where necessary.

The transmission circuitry 103 according to the first modification example repeats diffusion wave transmissions with different transmission angles and/or different transmission delay center points in units of packets through the ultrasonic probe 101 having multiple transducers. The transmission delay center point is an example of the transmission start point. The ultrasonic probe 101 according to the first modification example can be a linear probe, a convex probe, a sector probe, or a probe of any other alignment, which can transmit diffusion waves.

Figure 10:
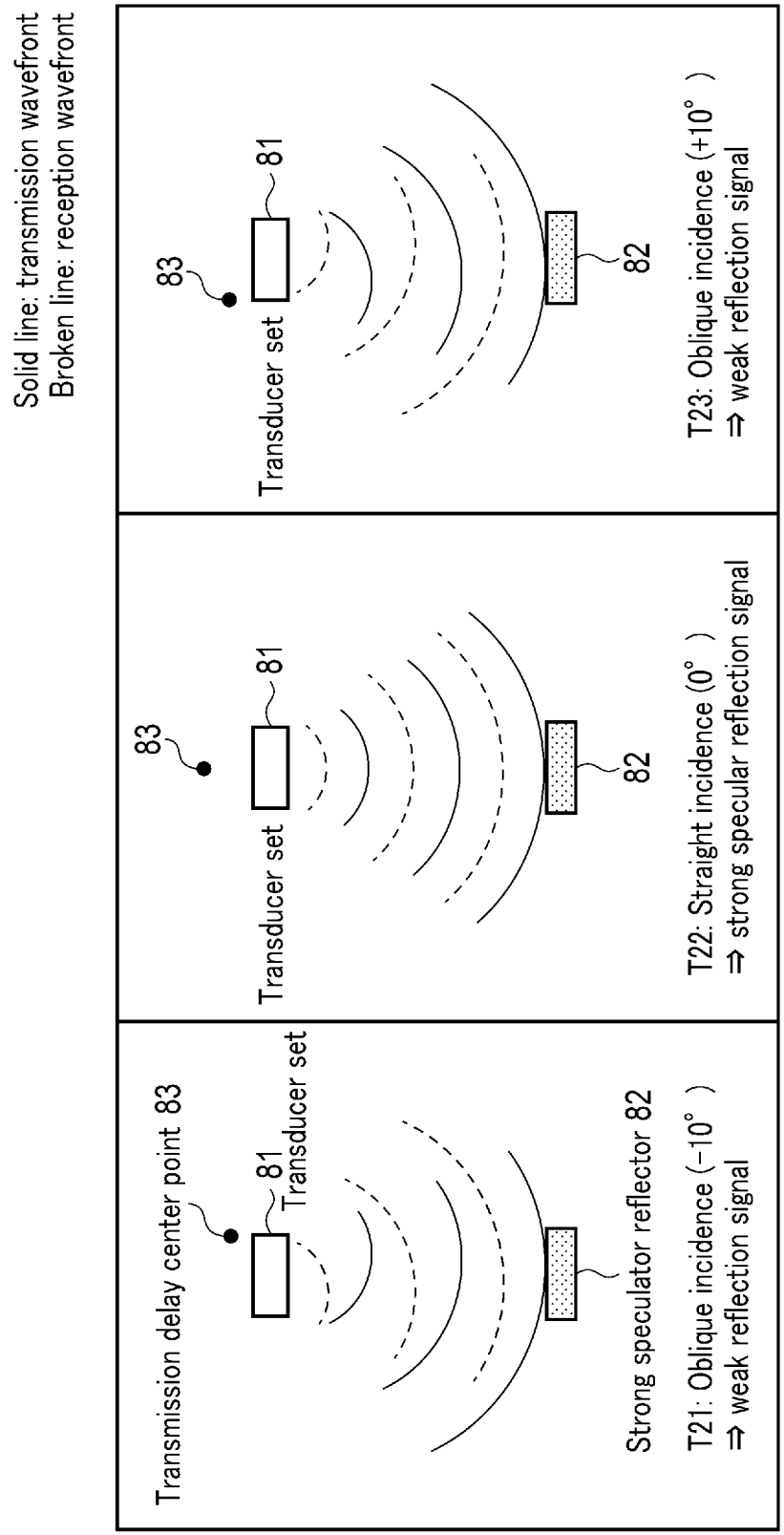
FIG. 10 is a diagram for explaining a diffusion wave transmission according to the first modification example.

FIG. 10 is a diagram explaining a diffusion wave transmission according to the first modification example. As illustrated in FIG. 10, a diffusion wave transmission refers to an ultrasonic wave transmission in which waves spread in the depth direction, as opposed to a plane wave transmission being an ultrasonic wave transmission in which waves do not spread in the depth direction. The transmission direction of the diffusion waves can be defined by the transmission angle and the transmission delay center point 83. The transmission angle can be defined by an angle formed by the central axis of the transmitted diffusion wave and the transmission surface of the transducer set 81. The transmission delay center point 83 is a virtual source of the diffusion wave transmission. The diffusion wave is transmitted from the transducer set 81 at any transmission angle, using the transmission delay center point 83 as a virtual wave source.

In the case of the transmission angle T22, where the transmission angle $\theta=0°$, or in other words when a diffusion wave generated by the transducer set 81 is incident straight upon the specular reflector 82, a specular reflection signal of a high intensity is generated, which causes specular reflector artifacts. In this case, the transmission delay center point 83 is positioned immediately above the central axis of the transducer set 81. In contrast, in the case of the transmission angle T21 or T23, where the transmission angle $\theta \ne 0°$, or in other words when the diffusion wave generated by the transducer set 81 is obliquely incident upon the specular reflector 82, a weak reflection signal is generated. The specular reflection signals, which exhibit a high dependency on angles, will not come out to be principal components among the reflection signals of the transmission angles T21 to T23. Thus, specular reflector artifacts can be reduced by performing principal component filtering on the MTI images.

The transmission delay center point 83 is positioned differently in accordance with the transmission angle. In the case of the transmission angle T21, the transmission delay center point 83 is determined to be at a lower right position on the drawing sheet in comparison to the case of the transmission angle T22, while in the case of the transmission angle T23, the transmission delay center point 83 is determined to be at a lower left position on the drawing sheet in comparison to the case of the transmission angle T22.

The ultrasonography according to the first modification example differs from the embodiment only in the ultrasonic wave transmission being changed from the plane wave transmission to the diffusion wave transmission, and the rest of the ultrasonography is the same as the embodiment. Thus, artifacts generated in blood flow images by specular reflection echo can be reduced with a small amount of calculation in the diffusion wave transmission as well.

Modification Example 2

In the embodiment and the first modification example, an initial image encompassing the entire target region is generated through pixel beamforming from a reception signal obtained from one ultrasonic wave transmission. According to the second modification example, an initial image encompassing the entire target region does not always need to be generated from a reception signal obtained from a single ultrasonic wave transmission. The beamforming circuitry 106 according to the second modification example generates an initial image relating to an overlapping area obtained from multiple ultrasonic wave transmissions with different transmission angles and/or different transmission origins. The ultrasonic wave transmission according to the second modification example is a distant focus transmission. The ultrasound diagnostic apparatus 100 according to the second modification example will be described below. In the explanation below, structural elements having substantially the same operations as the ones in the embodiment will be denoted by the same reference symbols, and the explanation of such elements will be given only where necessary.

The transmission circuitry 103 according to the second modification example repeats distant focus transmissions using different transmission angles and/or different transmission focal positions in units of packets through the ultrasonic probe 101 having multiple transducers. The transmission focal position is an example of the transmission start point. The direction of the distant focus transmission is defined by the transmission angle and the transmission focal position. The transmission angle is defined by an angle formed by the central axis of the transmitted ultrasonic wave and the transducer surface of the transducer set. The transmission focal position refers to the focal position of the transmitted ultrasonic wave set to a certain depth direction with respect to the transducer set. The distant focus transmission refers to an ultrasonic wave transmission for which the transmission focal position is set to a position deeper than the visual field depth. With a transmission focal position set to a position deeper than the visual field depth, a relatively flat sound field can be obtained. Even with such a sound field, specular reflector artifacts may still be generated. The ultrasonic probe 101 according to the second modification example can be a linear probe, a convex probe, a sector probe, or a probe of any other alignment, which can conduct a distant focus transmission.

The transmission circuitry 103 according to the second modification example performs multiple distant focus transmissions of different transmission focal positions in units of packets through the ultrasonic probe 101 having multiple transducers. The distant focus transmissions of each packet are determined to have transmission angles and/or transmission focal positions that differ from each other. Therefore, the reception areas respectively corresponding to the distant focus transmissions will differ in spatial positions. Here, the transmission focal position of each distant focus transmission is determined such that, among these reception areas corresponding to the distant focus transmissions, some of the reception areas spatially adjacent to each other will have an area overlapping each other. As a result of multiple distant focus transmissions, a large overlapping area can be obtained. The set of transducers used for an ultrasonic wave transmission (hereinafter referred to as a "set of driven elements") may be changed in accordance with the transmission focal position. For instance, the set of driven elements may be changed by shifting the set of elements selected from the set of transducers (transducer array) of the ultrasonic probe 101 sequentially from one end to the other end of the array. The ultrasonic scanning range can be further broadened in this manner.

Figure 11:
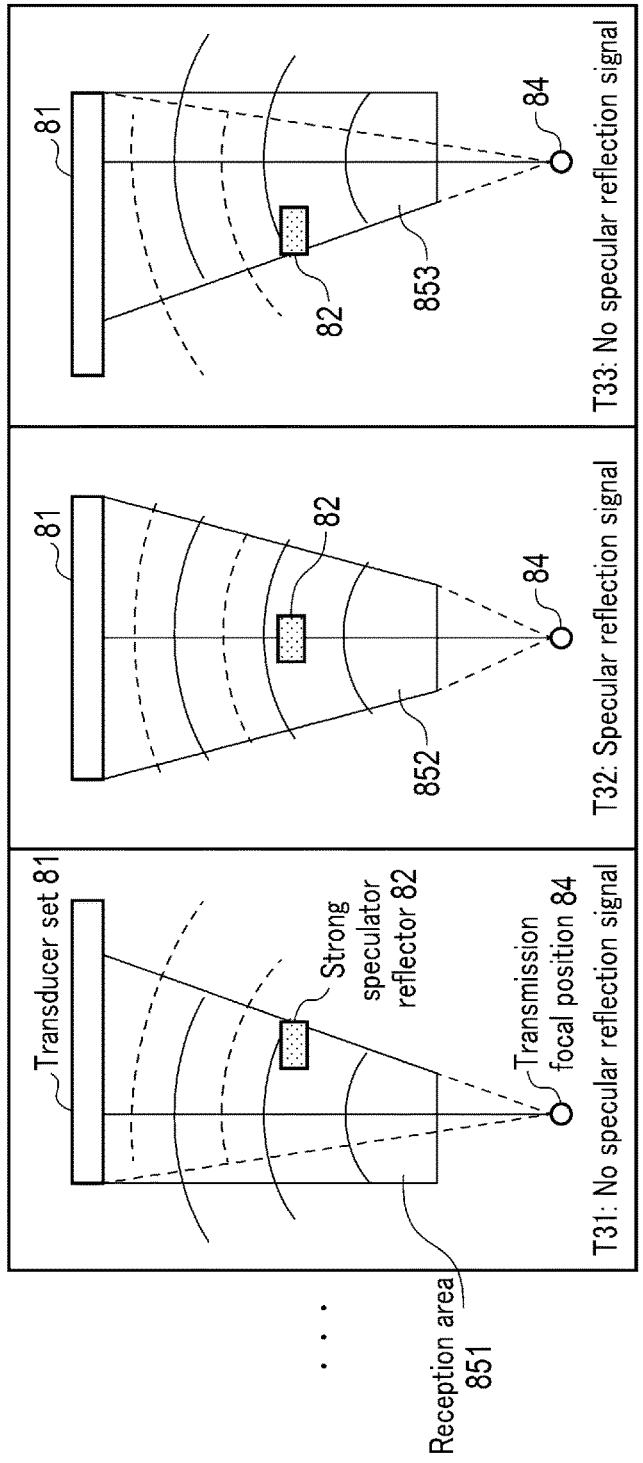
FIG. 11 is a diagram for explaining a distant focus transmission according to the second modification example.
Figure 11:
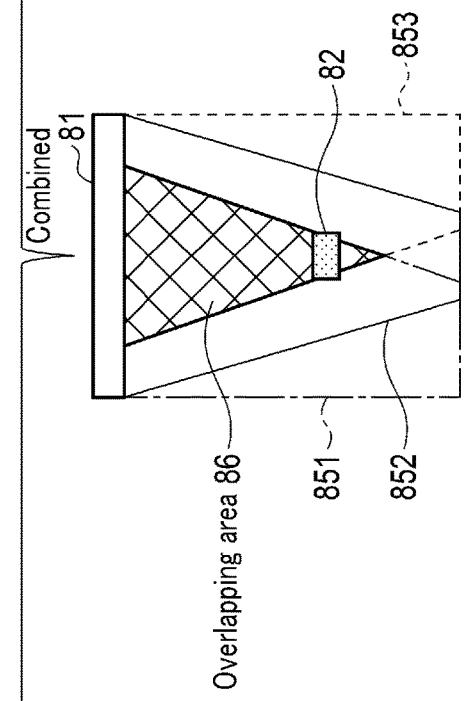

FIG. 11 is a diagram explaining a distant focus transmission according to the second modification example. Exemplary distant focus transmissions of three transmission directions T31, T32, and T33 included in one packet are illustrated in FIG. 11. In each of the distant focus transmissions, the transmission angles and transmission focal position 84 are determined such that the reception areas 851, 852, and 853 respectively corresponding to the distant focus transmissions T31, T32, and T33 will overlap each other. An overlapping area 86 can be obtained by combining the reception areas 851, 852, and 853.

As illustrated in FIG. 11, the region that contains the specular reflector 82 is included in the three reception areas 851, 852, and 853, where the angle of the transmission wavefront hitting the specular reflector 82 differs. For instance, in the transmission direction T32, the transmission wavefront hits the specular reflector 82 in a parallel manner, as a result of which a specular reflection signal is generated. With other transmission directions T31 and T33, the transmission wavefront obliquely hits the specular reflector 82, which means that no specular reflection signal is generated. The specular reflection signal, which is highly dependent on the angle, will not come out to be a principal component among the reflection signals of the transmission directions T31 to T33. Thus, specular reflector artifacts can be reduced by performing principal component filtering on the MTI images.

The beamforming circuitry 106 and Doppler processing circuitry 109 according to the second modification example performs a process similar to the one in the embodiment on the overlapping area of the reception areas that respectively correspond to the distant focus transmissions. Thus, artifacts generated in blood flow images by specular reflection echo can be reduced through a small amount of calculation. With the process performed on the overlapping area, an improvement in the signal-to-noise (S/N) ratio of a blood flow image can be expected, in comparison with the plane wave transmission and diffusion wave transmission. In relation to Equation (1), the number Nx of data items in the azimuth direction and the number Nz of data items in the depth direction are limited to data items within the overlapping area. The spatial position and range of the overlapping area are predetermined by a user or a system.

According to at least one embodiment described above, artifacts caused by specular reflection echoes in color Doppler imaging can be reduced through a small amount of calculation.

The word "processor" used in the above explanation may be, for example, a CPU, a GPU, an application specific integrated circuit (ASIC), a programmable logic device (e.g., Simple Programmable Logic Device (SPLD), Complex Programmable Logic Device (CPLD) field programmable gate array (FPGA)) or the like. The processor realizes functions by reading and executing a program stored in the memory circuitry. Instead of storing the program in the memory circuit, the program may be directly installed in the circuit of the processor. In this case, the processor realizes the functions by reading and executing the program installed in the circuit. If the process is an ASIC, the functions are directly installed in the circuitry of the processor as a logic circuit, instead of storing the program in the memory circuitry. The processors according to the embodiments are not limited to a single circuit for each processor, but may be configured as a single processor by combining different independent circuits to realize the functions. Furthermore, the structural components illustrated in FIG. 1 may be integrated into one processor to realize their capabilities.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus comprising:
   transmission circuitry configured to repeat a plurality of ultrasonic wave transmissions with different transmission angles and/or different transmission origins in units of packets by way of an ultrasonic probe including a plurality of transducers;
   reception circuitry configured to receive a plurality of reception signals corresponding to the ultrasonic wave transmissions by way of the ultrasonic probe;
   beamforming circuitry configured to perform beamforming respectively on the reception signals and generate a plurality of initial images;
   filtering circuitry configured to perform MTI filtering on the initial images for each group of the same transmission angle and/or the same transmission origin and generate a plurality of MTI images;
   principal component analysis circuitry configured to perform a principal component analysis on the MTI images for each of the packets having the same set of transmission angles and/or the same set of transmission origins and generate a plurality of principal component images; and
   coherent addition circuitry configured to perform coherent addition on the principal component images for each of the packets and generate a plurality of coherent addition images.

2. The ultrasound diagnostic apparatus according to claim 1, the apparatus further comprising:
   blood flow parameter calculation processing circuitry configured to perform a blood flow parameter calculation process on the coherent addition images and generate a blood flow image that represents a spatial distribution of a blood flow parameter.

3. The ultrasound diagnostic apparatus according to claim 2, the apparatus further comprising:
   processing circuitry configured to display the blood flow image on a display.

4. The ultrasound diagnostic apparatus according to claim 2, wherein
   the blood flow parameter calculation processing circuitry is configured to perform a power addition on the coherent addition images and generate as the blood flow image a blood flow power image that represents a spatial distribution of blood flow power that serves as the blood flow parameter.

5. The ultrasound diagnostic apparatus according to claim 1, wherein
   the transmission circuitry is further configured to repeat the ultrasonic wave transmissions in such a manner that spatial regions in which ultrasound waves are transmitted overlap each other across the ultrasonic wave transmissions.

6. The ultrasound diagnostic apparatus according to claim 1, wherein
   the transmission circuitry is further configured to perform, as the ultrasonic wave transmissions with the different transmission angles and/or the different transmission origins, a plurality of plane wave transmissions with different deflection angles.

7. The ultrasound diagnostic apparatus according to claim 1, wherein
   the transmission circuitry is further configured to perform, as the ultrasonic wave transmissions, a plurality of diffusion wave transmissions.

8. The ultrasound diagnostic apparatus according to claim 1, wherein
   the transmission circuitry is further configured to perform, as the ultrasonic wave transmissions, a plurality of distant focus transmissions.

9. The ultrasound diagnostic apparatus according to claim 1, wherein
   the beamforming circuitry is further configured to perform, as the beamforming, pixel beamforming, with which a complex pixel value of pixels located at the same spatial position is calculated regardless of the transmission angles and/or transmission origins.

10. The ultrasound diagnostic apparatus according to claim 1, wherein
    the filtering circuitry is further configured to perform the MTI filtering on only the initial images that belong to a certain number of packets preceding and including a current packet.

* * * * *